May 14, 1957 H. I. BURKEY Plant Pat. 1,601
SNAPDRAGON PLANT
Filed Sept. 5, 1956
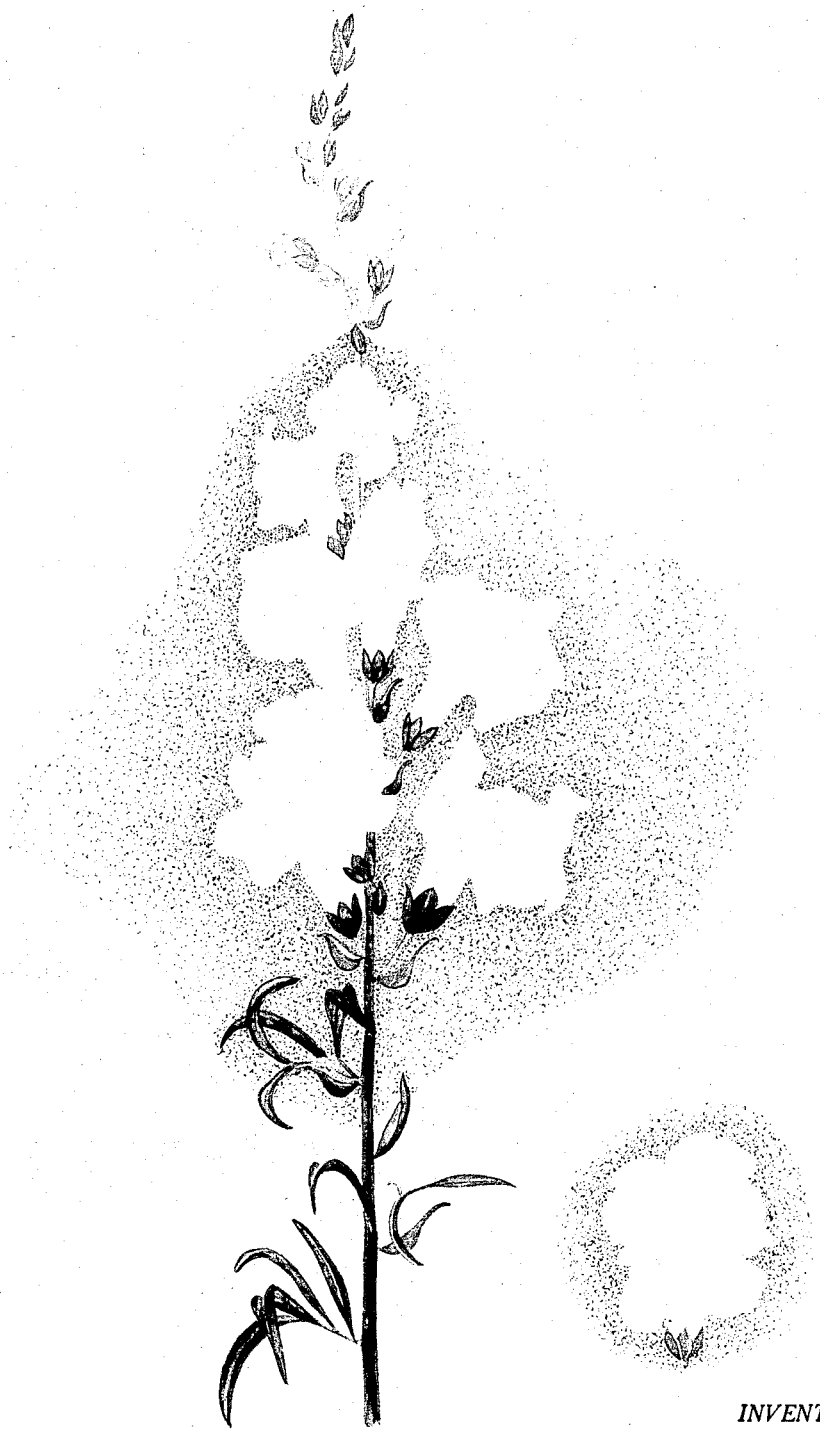
*INVENTOR.*
HAROLD IVAN BURKEY
*BY* Toulmin & Toulmin
ATTORNEYS United States Patent Office Plant Pat. 1,601
Patented May 14, 1957

1,601

SNAPDRAGON PLANT

Harold Ivan Burkey, Stuart, Fla.

Application September 5, 1956, Serial No. 608 176

1 Claim. (Cl. 47—60)

My present discovery relates to a new and distinct variety of snapdragon (Antirrhinum) plant which is a mutational variety from the variety of snapdragon plant shown and described in my Plant Patent No. 1,270, of April 20, 1954.

This new snapdragon plant is distinguishable from the parent plant mainly in the color of its blossoms. The flowers are of a distinctly white coloration.

This new variety has been asexually reproduced by cuttings in my greenhouses and farm in Stuart, Florida, and has remained true to type and the therein described characteristics through the propagation of over 700 plants during the period of six months. There are presently 700 plants in existence at my farm in Stuart, Florida. No seeds have been produced by this new variety so all propagation must be asexual.

Like the parent plant this new variety of snapdragon shows a pronounced reduplication of its petal-like parts and is sharply distinguished from other double snapdragons by the profusion of blossoms; the absence of excessive lateral shoots; the variety is vigorous and easy to propagate; has a hard stiff stem and exhibits a fragrance.

The accompanying illustrations show in full color a view embodying the invention and a smaller front view of the flower of the new variety.

Referring to the illustrations, the upper petal lobes, which are integral with the corolla tube, are oppositely disposed, two in number, curl backwardly, are of substantially equal size and have their center edges overlapping; the lower petal lobes are three in number, curl backwardly to partially cover the corolla tube, are crinkled on the edges and overlap each other slightly.

True functional stamens are not present but the usual six to eight stamens bear at their upper ends small white wrinkled petals; approximately one-half of these stamens, usually those on the lower lobes, have light yellow markings which extend up to the white of the small petals and set off the distinctive white coloration of the petals.

The plant has a hard, stiff stem, and the length of the stem and of the spike vary with conditions such as weather and age; at maturity the stem may have a considerable height, a length of six feet not being unusual, as in the parent plant. The leaves are arranged irregularly alternately around the stem; the flowers are closely grouped and present a compact appearance.

The upper end of the spike has a plurality of flower buds with accompanying bracts and these progressively open as the variety ages. In the embodiment of the invention illustrated the spikes are somewhat short as the illustration was made at a time somewhat before full growth had been attained.

As shown in the drawings, and particularly in the smaller figure, the corolla tube which carries the petal lobes has in the lower portion a yellowish-amber tint similar to that found in the petal, which tint is emphasized if, as occasionally happens, a number of the corolla tubes are in close visible proximity.

The white of the corolla tube is tinted with a yellowish hue which emerges into the distinctive and characteristic white of the petals. The petals themselves are slightly darker in the center than in the body and give to the variety the distinctive white coloration. The yellow-nonfunctional stamens protrude centrally of the flower and enhance the overall appearance.

The color designations of the variety, according to: "A Dictionary of Color," by Maerz and Paul, are as follows:

| | Plate | Letter | Number |
|---|---|---|---|
| Main flower color lobes | 10 | B | 1 |
| Edge coloration of the lobes | 10 | B | 1 |
| Petals or stamens | 10 | D | 1 |
| Stamen markings | 9 | J | 1 |
| Corolla tube | 9 | B | 2 |
| Stem | 21 | G | 4 |
| Sepals | 21 | K | 6 |
| Leaves | 21 | K | 9 |

Having thus disclosed my discovery, I claim:

A new and distinct variety of double snapdragon plant characterized particularly by its pleasing, distinctive characteristic white coloration of the flowers; the compactness of the flowers; the absence of excessive lateral shoots; and its vigor and hard stiff stems.

No references cited.